US006665430B2

(12) United States Patent
Reynolds et al.

(10) Patent No.: US 6,665,430 B2
(45) Date of Patent: Dec. 16, 2003

(54) FLUORESCENCE DIGITAL IMAGING MICROSCOPY SYSTEM

(75) Inventors: C. Patrick Reynolds, Sherman Oaks, CA (US); Tomas Frgala, Brno (CZ)

(73) Assignee: Childrens Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 10/217,721

(22) Filed: Aug. 13, 2002

(65) Prior Publication Data

US 2002/0191824 A1 Dec. 19, 2002

Related U.S. Application Data

(60) Division of application No. 09/066,134, filed on Apr. 24, 1998, now Pat. No. 6,459,805, which is a continuation-in-part of application No. 08/622,110, filed on Mar. 26, 1996, now abandoned.

(51) Int. Cl.[7] ................................................. G06K 9/00
(52) U.S. Cl. ............................ 382/128; 435/6; 435/29; 435/40.5
(58) Field of Search ............................... 382/100, 128, 382/129–134; 424/400, 145.1; 435/23, 226, 6, 69.1, 29, 183, 173.3; 514/12; 530/350

(56) References Cited

U.S. PATENT DOCUMENTS

| 4,933,471 A | | 6/1990 | Lee ................................ 549/33 |
| 4,937,159 A | | 6/1990 | Gottschalk et al. ......... 430/138 |
| 5,018,209 A | | 5/1991 | Bacus ......................... 382/128 |
| 5,175,092 A | * | 12/1992 | Gabriels, Jr. ................. 435/29 |
| 5,369,566 A | | 11/1994 | Pfost et al. ................. 382/128 |
| 5,403,721 A | * | 4/1995 | Ward et al. .................... 435/34 |
| 5,434,076 A | * | 7/1995 | Freedman et al. .......... 435/344 |
| 5,516,629 A | * | 5/1996 | Park et al. ...................... 435/2 |
| 5,578,442 A | * | 11/1996 | Desai et al. ................. 435/1.1 |
| 5,658,751 A | | 8/1997 | Yue et al. .................... 435/34 |
| 5,693,484 A | | 12/1997 | Nakamoto et al. ............ 435/34 |
| 5,733,524 A | * | 3/1998 | Bucala et al. ................. 424/9.2 |
| 5,763,181 A | * | 6/1998 | Han et al. ........................ 435/6 |
| 5,843,743 A | | 12/1998 | Hubbell et al. .............. 435/177 |
| 5,849,578 A | * | 12/1998 | Falb ............................ 435/325 |
| 5,945,283 A | | 8/1999 | Kwok et al. .................... 435/6 |
| 5,955,256 A | * | 9/1999 | Sowemimo-Coker et al. . 435/2 |
| 6,077,519 A | * | 6/2000 | Storkus et al. ............ 424/277.1 |
| 6,160,617 A | * | 12/2000 | Yang .......................... 356/300 |
| 6,261,596 B1 | | 7/2001 | Li et al. ...................... 424/450 |
| 6,277,655 B1 | | 8/2001 | Sarkadi et al. .............. 436/536 |

OTHER PUBLICATIONS

Lakowicz et al., "Advances in Fluorescence Sensing Technology", SPIE Proceedings, vol. 1885, Univ. of Maryland, Baltimore, MD. Jan. 17, 1993, pp. 1–27.*

Lakowicz et al., "Time–Resolved Laser Spectroscopy in Biochemistry III", SPIE Proceedings, vol. 1640, Univ. of Maryland, Baltimore, MD, Jan. 19, 1992, pp. 1–52.*

* cited by examiner

Primary Examiner—Jayanti K. Patel
(74) Attorney, Agent, or Firm—Hogan & Hartson LLP

(57) ABSTRACT

A method of preparing cell samples for viable cell number quantification with a fluorescence digital imaging microscopy system employing digital thresholding technique. The cell sample is stained with a first, fluorescent dye and treated with a second dye that is able to quench the fluorescence of the first dye. The fluorescent dye accumulates in viable cells only and is used to stain the viable cells. The second dye is excluded from viable cells but enters non-viable cells, thereby quenching the background fluorescence in non-viable cells and the medium. Two examples of dye combinations are described: fluorescein diacetate used as the fluorescent dye with eosin Y as the quenching dye; and calcein-AM used as the fluorescent dye with trypan blue as the quenching dye. By reducing the background fluorescence, the dynamic range and accuracy of viable cell number measurements are enhanced. In low viability cultures treated with fluorescein diacetate, background fluorescence completely masked viable cells, but digital thresholding and eosin treatment dramatically reduced background fluorescence, producing a linear response over 4 logs of viable cell density.

9 Claims, 13 Drawing Sheets

Stage Object Edit Screen

| | |
|---|---|
| File Description: | *Falcon 3072. 96 Wells* |
| Path: *c:\stage* | Filename: *96falcon* |
| Number of wells: | Horiz: *12* Vert: *8* Tot: *96* |
| Shape of wells: | *Round* |
| Length of vertical edge: | *0.00* mm |
| Length of horizontal edge: | *0.00* mm |
| Inside diameter of well: | *6.20* mm |
| | |
| Distance between two wells, horiz.: | *2.78* mm |
| Distance between two wells, vert.: | *2.80* mm |
| Dist. – left of plate to left of first well: | *0.00* mm |
| Dist. – top of plate to top of first well: | *0.00* mm |
| Dist. – left of plate to left of ref. point: | *6.90* mm |
| Dist. – top of plate to top of ref. point: | *7.38* mm |
| Instructions for aligning reference point: | *Align "B" of "B2" printed on plate with left and top edges of monitor. Set Home to zero.* |

FIG. 2

Assay Edit Screen

Assay: *These 3 lines are for describing the assay such as type of dye, conditions, etc.*
Assay path: *c:\assay* File: *Testname*
Plate: *Falcon 3072. 96 Wells*
Plate path: *c:\stage* File: *96falcon*
Output path: *c:\date* File: *Testname*

Number of wells:     Horiz: *12*    Vert: *8*
Beginning position:  Horiz: *1*     Vert: *1*
Well scan:                    *Underscan*
Pixel summation:   *Total Fluorescence*

Assay start date/time: 06/22/93     *10:45*
Current date/time:     06/29/93     *13:15*
Plate registration:    *Align "B" of "B2" printed on plate with left and top edges of monitor. Set Home to zero.*

FIG. 3

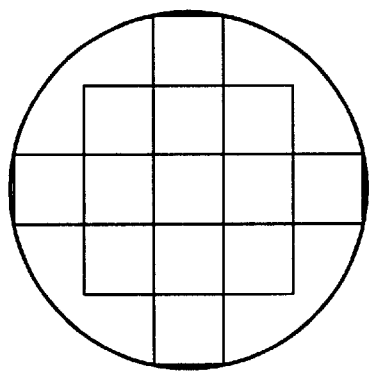
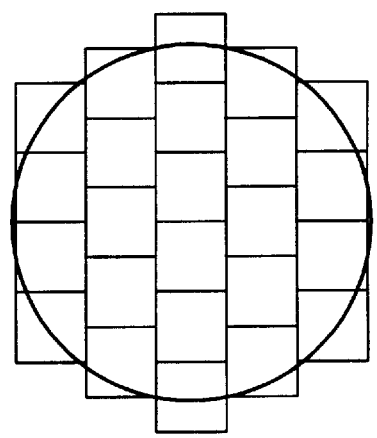
FIG. 4a        FIG. 4b

| Optimized Frame Summation Pseudocade |
|---|
| For all the Wells<br>   Check Motors from Previous Move<br>      Wait if still moving<br>   Grab and Freeze Current Frame<br>   Issue Move command for next Frame<br><br>   {Sum the Current Frame}<br>   For Video_Buffer = 0 to 3<br>     Base = $D000_{hex}$<br>     For Segment = 0 to<br>        (Segments per Video Buffer)/8<br>      {Sum 8 segments, hardcoded}<br>      Sum = Sum + Mem[Base:$00_{hex}$]+<br>                      Mem[Base:$01_{hex}$]+<br>                      Mem[Base:$02_{hex}$]+<br>                      Mem[Base:$3F_{hex}$]<br>     Base = Base + 8<br>   $Sum_{longint}$ = $Sum_{longint}$ + Sum |

FIG. 6

Analysis Menu

| | | | | |
|---|---|---|---|---|
| 1. | 96 Wells. | 6 Groups of | 2 Across x | 8 Down |
| 2. | 96 Wells. | 3 Groups of | 4 Across x | 8 Down |
| 3. | 96 Wells. | 2 Groups of | 6 Across x | 8 Down |
| 4. | 96 Wells. | 6 Groups of | 4 Across x | 4 Down |
| 5. | 96 Wells. | 12 Groups of | 1 Across x | 8 Down |
| 6. | 96 Wells. | 8 Groups of | 12 Across x | 1 Down |
| 7. | 96 Wells. | 4 Groups of | 12 Across x | 2 Down |
| 8. | 96 Wells. | 24 Groups of | 2 Across x | 2 Down |
| 9. | 24 Wells. | 2 Groups of | 3 Across x | 4 Down |
| A. | 24 Wells. | 2 Groups of | 6 Across x | 2 Down |
| B. | Convert to Comma Separated Format (CSV) | | | |
| E. | Edit Bad Data Points | | | |

FIG. 8

FLUORESCENCE DIGITAL IMAGING MICROSCOPY SYSTEM

This is a divisional of application Ser. No. 09/066,134 filed Apr. 24, 1998, now U.S. Pat. No. 6,459,805 which is a continuation-in-part of prior application Ser. No. 08/622,110 filed Mar. 26, 1996, now abandoned which applications are hereby incorporated by reference in their entirety.

BACKGROUND OF THE INVENTION

1. Field of the Invention

This invention relates to a system for quantifying relative cell numbers in tissue culture containers, and more particularly to a system for quantifying relative cell numbers in tissue culture containers using fluorescence digital imaging microscopy.

2. Description of the Prior Art

Measurement of relative cell numbers (total and/or viable only) is necessary for a wide variety of biological, immunological, and therapeutic studies and often requires analyzing many replicate samples. The use of multi-well tissue culture plates, such as the 96-well plates, provides a convenient format for such assays. Microwell assays for relative cell number have used radioactive isotopes ($^{51}Cr$ release or $^3H$ thymidine incorporation), colorimetric substrates produced by viable cells (MTT), or fluorescent dyes that accumulate in viable cells (fluorescein diacetate) or all cells (Hoechst 33342, ethidium bromide, etc.). Assays using radioactive isotopes require specialized waste disposal and the risk of exposure to radioactivity, while calorimetric assays may provide less precision or dynamic range than isotopic assays. Assay systems using fluorescent dyes are particularly attractive because of their ease of use, lack of radioactive waste, short incubation times, and because of the ability to rapidly measure cell numbers directly without disrupting cells.

Measuring the fluorescence of a sample involves illuminating the sample with light of suitable wavelengths, and recording the intensity of the fluorescence produced by the sample. Fluorescence readers that are currently commercially available use a photomultiplier tube to directly measure total fluorescence in a well, without using a focusing mechanism to measure the fluorescence of defined areas of a well. Since photomultiplier tubes detect total fluorescence, they cannot discriminate between background fluorescence and intracellular fluorescence. Consequently, assays must rely on rinsing steps to eliminate background fluorescence.

Furthermore, existing fluorescence readers have limited flexibility. For example, the Baxter Pandex FCA required the use of custom Pandex plates to wash the cells and an internal bead standard using custom Fluoricon reference beads. Therefore, existing florescence readers offer poor flexibility, low sensitivity and dynamic range, especially when background fluorescence is high.

Another limitation of commercial fluorescence readers and existing methods for quantification of cell number is the inability to discriminate between the fluorescence from the viable cells and background fluorescence in the wells from dye in the medium and dead cells.

SUMMARY OF THE INVENTION

It is an object of this invention to provide a high degree of sensitivity and dynamic range for measurements of the number of viable cells.

It is a further object of the invention to provide a high degree of sensitivity and dynamic range for viable cell number measurements in the presence of large numbers of non-viable cells.

It is a further object of the invention to create a system for quantifying cellular fluorescence in situ, using a variety of tissue culture plate formats.

In response to these goals, a computer-controlled digital imaging microscopy scanning system is developed as described herein. The system is configured to accommodate a variety of tissue culture plates. Focusing optics are used to form an image of a defined area of the plate, which image is recorded by a recording device and digitized. The digital image, in the form of fluorescence light intensity at each pixel of the image, is then manipulated by the computer software to reduce background noise and extract desired information. The plate is mounted on a motorized stage, the movement of which is controlled by the computer. As the stage moves according to the computer commands, a series of images, or frames, are recorded, the frames covering the wells to be measured. This is referred to as a scan. During such a scan, the movement of the stage, the recording and digitizing of the images and the extraction of information occur in a synchronized manner under computer control.

The stage is designed to accommodate tissue culture plates of various formats, and the computer software is designed to control the stage movement for scanning the plate according to the format inputted to the computer. The algorithm for automatic determination of the scanning movement is described in more detail hereinafter.

The software quantifies fluorescence for the sample according to a predetermined method, described in more detail hereinafter, and sends the results both to the computer screen and to a data file. The software allows for two types of calibration, and provides easy to use menus for entering configuration, calibration and assay parameters, or data analysis specifications.

For the purpose of relative cell number determination, total fluorescence of a well is obtained by summing the fluorescence light intensities of all pixels in all frames for the well. The software provides for thresholding ability to enhance signal and reduce noise in the digital images. For example, fluorescence light intensities that are below a predetermined threshold may be rejected by using a Look Up Table. Because intracellular fluorescence is concentrated in a small area and is more intense, while background fluorescence is much more diffuse and is less intense, thresholding effectively reduces the background noise and increases the dynamic range of the cell number measurement. For samples with high background fluorescence, this technique accomplishes cell number measurement in one step, and eliminates the need for extra steps, such as rinsing, which would be otherwise required to reduce background fluorescence.

A method is also described for enhancing the dynamic range and accuracy of viable cell number measurements by treating the sample with a second dye to quench background fluorescence from the medium and non-viable cells. The first (fluorescent) dye accumulates in viable cells, while the second (quenching) dye enters non-viable cells but not viable cells, thereby quenching the fluorescence of the first dye in non-viable cells and the medium. When fluorescein diacetate (FDA) is used as the fluorescent dye, eosin Y (2'4'5'6'-Tetrabromofluorescein) may be used to quench the background fluorescence. When calcein-AM (Glycine, N,N'-[[3',6'-bis(acetyloxy)-3-oxospiro[isobenzofuran-1 (3H),9'-[9H]xanthene]-2',7'-diyl]bis(methylene)]bis[N-[2-[(acetyloxy)methoxy]-2-oxoethyl]]-, bis(acetyloxy)methyl]

ester) (Molecular Probes, Inc., Eugene, Oreg.) is used as the fluorescent dye, trypan blue (3,3'-[3,3'-Dimethyl[1,1'-biphenyl]-4,4'-diyl)bis(azo)]bis[5-amino-4-hydroxy-2,7-naphthalene-disulfonic acid] tetrasodium salt) may be used to quench the background fluorescence.

BRIEF DESCRIPTION OF THE DRAWINGS

FIG. 2 is the Stage Object Edit screen of the control software of the fluorescence digital imaging microscopy system.

FIG. 3 is the Assay Edit screen of the control software of the fluorescence digital imaging microscopy system.

FIG. 4 illustrates two scan patterns for a well. FIG. 4(A) shows underscanning, in which all frames remain within the boundaries of each well. Some portions of the well are not imaged with this method. FIG. 4(B) shows overscanning, in which frames extend beyond the boundaries of each well, but image the entire area of the well.

FIG. 6 is a segment of the software in pseudocode which illustrates optimization of stage movement and frame summation.

FIG. 8 is the Analysis Menu screen of the control software of the fluorescence digital imaging microscopy system.

DESCRIPTION OF THE PREFERRED EMBODIMENT

Hardware

Figure 1:
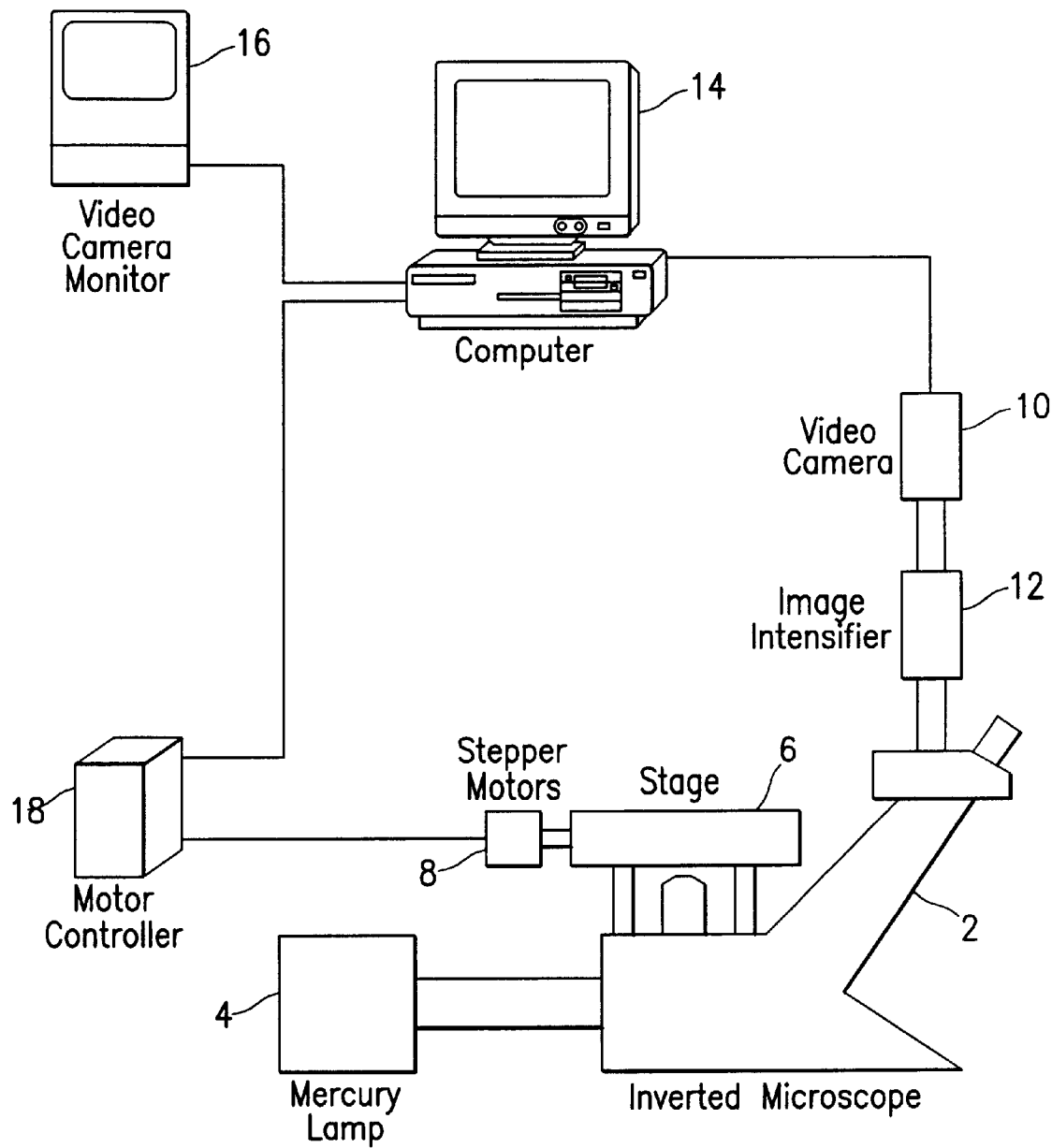
FIG. 1 is a diagram that illustrates the overall configuration of the preferred embodiment of the fluorescence digital imaging microscopy system of the present invention.

The overall configuration of the preferred embodiment of the present invention is illustrated in FIG. 1. An Olympus CK-2 inverted microscope 2 is configured for epi-illumination with a 100 Watt mercury vapor lamp 4 (HBO-100), fitted for Olympus IMT-style filters. The stage 6 of the inverted microscope 2 has an opening which is modified to fit various tissue culture plates, including 96-well, 24-well, and 6-well formats (McBain Instruments, Chatsworth, Calif.). Vexta stepper motors 8 (Oriental Motor Company, Japan, available from McBain Instruments) are mounted on the stage for providing movements of the stage in two horizontal directions, the X and Y directions. Stepper motor resolution is 12,500 steps per revolution, and lead screw pitch is 1.0 mm. A Cohu (San Diego, Calif.) model 4815-2000 monochrome video camera 10 with the Automatic Gain Control (AGC) jumper disabled is attached to the standard trinocular head of the inverted microscope 2 with an 80/20 beam splitter. A KS-1381 image intensifier 12 (VideoScope International, Sterling, Va.) may be installed between the trinocular head and the video camera. The above hardware subsystems are readily available from commercial sources.

The digital imaging microscopy system of the present invention is controlled by a computer 14. In the preferred embodiment, the computer system comprises a Hewlett-Packard Vectra microcomputer with a 25 Mhz 80386 processor running MS-DOS 3.3, 2 megabytes of memory, VGA graphics, Microsoft mouse, and an Ultrasync color monitor (Princeton Graphic Systems, Princeton, N.J.). A PC-Vision imaging board (Imaging Technology, Woburn, Mass.) is used for video capture with output to a PM970 monochrome monitor 16 (Ikegami, Maywood, N.J.) on the BNC "green" cable. The PC-Vision board provided 512×480 pixel resolution and 256 gray levels per pixel with standard video output at 30 frames per minute. Stepper motors are guided by a Compumotor (Parker-Hannifin, Petaluma, Calif.) PC-23 controller board and two Compumotor C-Drive controllers 18.

Optical filters are readily available for the standard Olympus IMT mount and are as follows: For Hoechst 33342 either an Olympus "U" IMT cube, or an Omega Optical (Woburn, Mass.) XF05 filter set (excitation 345 nm, emission 475 nm). For FDA and BCECF-AM either an Olympus "B" IMT cube, or an Omega Optical XF22 filter set (excitation 490 nm, emission 525 nm) (22). Omega Optical filters have a special coating to eliminate infrared interference. For Olympus filters without the special coating, an Omega Optical BG1 filter is placed in front of the excitation filter on the IMT filter block to eliminate infrared emissions.

Software

In the preferred embodiment, the digital imaging microscopy system is controlled by a software developed with Turbo Pascal 6 (Borland, Scotts Valley, Calif.). Text mode windows, menus, and dBASE™/FoxPro™ file compatibility are provided by TOPAZ (Software Sciences, Burlingame, Calif.), a library of screen and database primitives. Sigma-Plot™ (Jandell Scientific, San Rafael, Calif.) is used to create graphs and calculate coefficients of correlation. Standard deviation is calculated by the software.

To provide for greater flexibility, the software program stores system and assay specific information in data files. Parameters relating to size, shape, and number of wells are stored in individual "stage object" files. System specific information, such as type of video board, jumper settings, I/O addresses, and stepper motor specifications, is stored in a configuration file while specifications describing individual assays are stored in separate assay files. With this generalized design, the software can be quickly adjusted for changes in the hardware.

As described in more details hereinafter, the software automatically calculates the proper stage position for all readings, moves the stage and quantifies each frame of fluorescence image in a synchronized manner, and quantifies relative fluorescence for each well.

Parameter Input and Operation

The software provides for input of various control parameters necessary to control the system operation. Tissue culture plate parameters are inputted to the system through the Stage Object Edit screen, as shown in FIG. 2. This screen allows the user to enter the number of wells vertically and horizontally, the shape of the wells (round or square), the well dimensions (diameter, or sides in mm), the distance between wells in mm, and the reference point. The reference point can be any easily identified position on the tissue culture plate which can be used to align the plate in the video monitor. Plates are described to the system only once and then become part of a plate selection menu. At the time an assay definition is created the user simply selects the plate from a menu of plate choices. Thus, nearly any format of a tissue culture container can be described to the system, including 96-well, 24-well, and 6-well plates, individual 35 mm dishes, and 25 cm² flasks. These parameters are stored in individual "stage object" files.

The user enters assay parameters through the Assay Edit Screen, shown in FIG. 3. Specifications are stored in individual assay files. The user can enter a description for the assay and filenames for both the assay file and the data output file. When the "Plate" item is highlighted a menu appears allowing selection of a tissue culture plate from a list of those which have already been described to the system. If the number of wells to be scanned is less than the total number of wells in the plate, the user can modify both the number of wells desired and the initial well to be scanned.

The "Well Scan" item allows for selection of scanning mode: Underscan or Overscan. Underscanning selects the video frames which are completely contained within each well, even though some areas of the well are not covered. Overscanning allows every portion of the well to be covered even though this results in portions of some frames falling outside the boundaries of the well. FIGS. 4(A) and 4(B) illustrate Underscanning and Overscanning, respectively. Underscanning is generally selected when speed is important while Overscanning is selected when it is important to scan the entire well, for example, to ensure detection of small numbers of cells. Switching between Underscanning and Overscanning simply involves changing the setting on the Assay Edit Screen.

The next item, "Pixel Summation," controls the way in which video images are treated. For example, using the "Total Fluorescence" function, the values of all pixels in each video frame are summarized, yielding a single intensity value for each well scanned. Assay Start Date/Time and Current Date/Time may be modified as needed. They are logged to the data file each time the assay is performed, so results may be taken over multiple time periods. For this type of assay, results are stored together in one data file which can later be used to plot the change in fluorescence intensity over time.

A "Plate Registration" section also appears on the Assay Edit Screen. This is a descriptive section in which information specific to the type of tissue culture plate is displayed in a read-only fashion, describing the proper alignment for the type of plate. Instructions vary for different types of tissue culture plates. For example, 96-well plates may be marked A1, A2, A3, B1, B2, B3, etc., while 6-well plates are numbered 1 through 6. The user adjusts the stage manually with the arrow keys, aligns the plate, and begins the assay. The system then controls the stage and scans the plate according to the selections made by the user.

Occasionally, artifacts appear in a well, such as highly autofluorescent foreign objects. The user can mark these wells as bad data points during the assay by pressing the Space bar, and the data point is eliminated from further analysis. Alternatively, individual wells may be excluded from analysis after the assay is completed by selecting a special edit function from the menu.

Calibration

Prior to scanning plates the system is calibrated. There are two types of calibrations: daily and frame-to-stage calibration. Daily calibration involves adjusting the fluorescence intensity of the microscope through the use of standard beads prior to an assay. It consists of adding two drops of Hoechst beads (Flow Cytometry Standards, Research Triangle Park, N.J.) to 1.0 ml distilled water in a microfuge tube, mixing thoroughly by shaking, and loading into a column (eighth wells) of a 96-well plate, 100 µl per well. Wells are scanned and the microscope aperture diaphragm is adjusted repeatedly until the fluorescence intensities per well are within the desired range.

Frame-to-stage is performed only when there is some physical change to the microscope setup, such as changing the magnification, adding or removing the image intensifier, or changing the type of culture plate to be analyzed. This calibration involves correlating the image on the screen, in pixels, to the physical size of the same area on the stage, in millimeters. To perform the calibration, the user places an etched-glass micrometer on the stage so that the image of the micrometer appears on the video monitor. The calibration routine superimposes horizontal and vertical hatch marks on the image of the micrometer every 50 pixels. The user then aligns the micrometer marks with the hatch marks by moving the stage with the arrow keys and by entering the number of pixels equal to a specific distance on the micrometer. For both X and Y directions, the system automatically calculates pixels per millimeter, and stores this information in the system configuration file.

Scanning Algorithm

Figure 5:
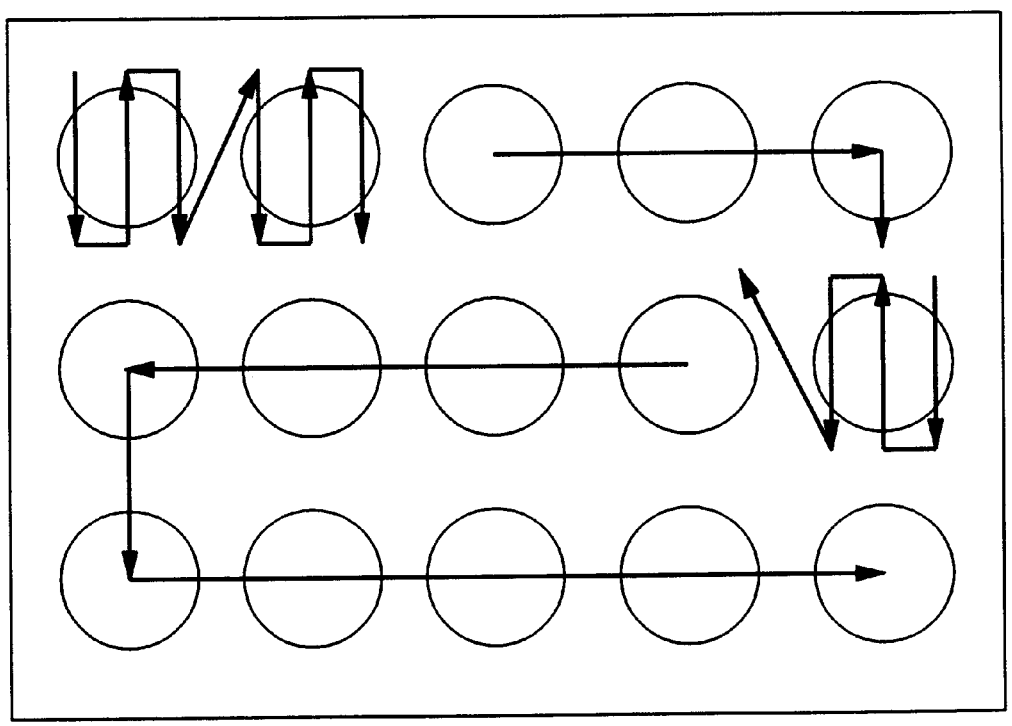
FIG. 5 is a plate scanning diagram which illustrates the direction of the scan for a multiwells plate. The overall direction of travel varies depending on each row. In this example, odd rows are traversed towards the right while even rows are traversed to the left.

Referring to FIG. 5, in the preferred embodiment of the present invention, tissue culture plates are scanned with a serpentine, or back-and-forth motion, left and right across rows and up and down within individual wells. The scanning pattern for the entire plate is automatically determined by the system. Based on the calibration information, specifications in the stage object and assay files, and the algorithm described below, the program calculates the number of video frames required to scan each well and their position, storing all the information needed to control the stage and camera for the entire tissue culture plate in a command file.

In the preferred embodiment, the algorithm for mapping individual video frames to individual microplate wells is as follows. The diameter of the well for a round well, or the sides for a rectangular well, are known from the predetermined values in the Stage Object File. The width of the video frame is calculated from the well diameter and the calibration value in pixels per millimeter. The system determines the number of frames in the horizontal direction and centers them in the well. Then, for each of the horizonal frames, the system determines the number of vertical frames required for that particular "slice" of the well and centers them vertically. FIGS. 4(A) and 4(B) are examples of individual frames mapped to a well. Once all the frame positions for one well are determined, the beginning position of the next well is calculated, and the process repeats for the remaining wells in the plate.

Quantification of Fluorescence

The software quantifies relative cell numbers by analyzing the pixel intensities of the images digitized from the video camera. The PC-Vision board provides 256 intensity levels for each pixel; the brighter the fluorescence, the higher the numerical value. Total fluorescence per well should be directly proportional to total cell number when the supravital DNA-staining dye Hoechst 33342 is used, and to viable cell number when FDA or BCECF is used. By summing the pixel intensities for all the video frames covering a well, the software determines the total relative fluorescence intensity for the entire well, which is proportional to cell number.

Programming Techniques to Minimize Plate Scanning Time

Two programming techniques are employed to minimize the time for scanning a plate. First, as shown by the pseudocode in FIG. 6, the program is organized so that stage movement takes places concurrently with the summation of the current video frame, producing a pseudo multi-tasking effect. The software freezes the video frame, issues the stage movement command, and sums the pixels in the frame while the stage is physically in motion.

Second, a more efficient usage of certain Turbo Pascal instructions is designed to access memory directly which resulted in much faster summation of pixels. In the 80386 microchip, memory is addressed by Base, and Offset. The Base Address describes a certain segment in memory, and the Offset gives a certain offset from that segment. In Turbo Pascal, the specific instruction is: Mem[Base:Offset]. As shown in FIG. 6, in calculating the summation, the Base is incremented while the Offset is kept constant. The Base is incremented by eight in FIG. 6 because the absolute offsets, $00_{hex}$ to $3F_{hex}$, correspond to eight segments. This is significantly faster than a simple looping algorithm in which the Base Address remains constant and the Offset is incremented.

Thresholding

Digital thresholding is used to distinguish desired intracellular fluorescence from unwanted background fluorescence. Because intracellular fluorescence is concentrated in a small area and is more intense while background fluorescence is much more diffuse and is less intense, contribution to the total fluorescence measurement from background fluorescence is reduced by ignoring light intensities which are below a specified value.

Figure 7:
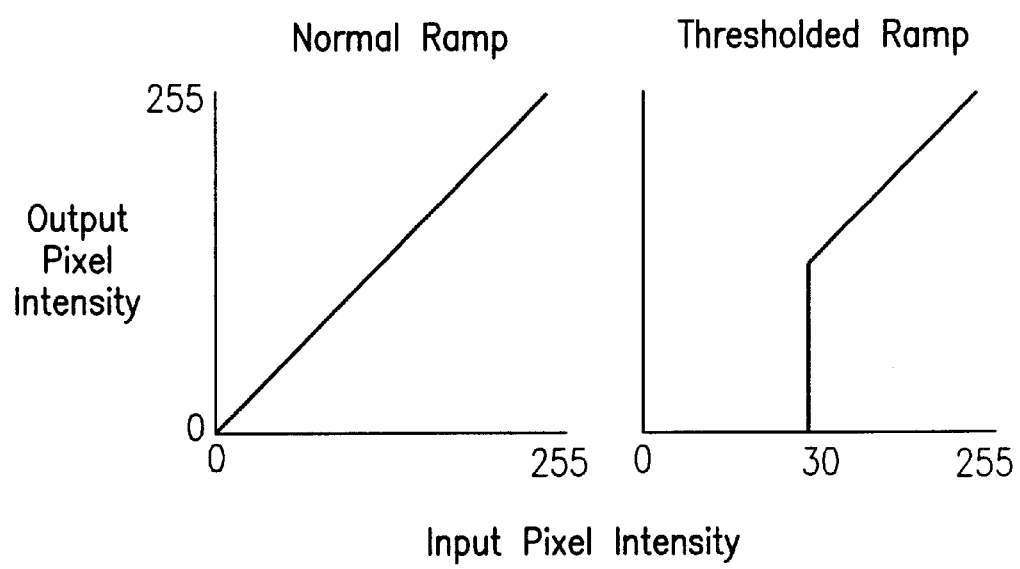
FIG. 7 illustrates image thresholding.

In the preferred embodiment of the present invention, thresholding is accomplished by changing the default values stored in a Look Up Table (LUT) in the imaging hardware within the PC-Vision board. Pixel intensities which enter the hardware are compared against the LUT, and output intensities are assigned. By altering the values in the LUT, the output intensities can be changed. Referring to FIG. 7, in a normal LUT, every output value is the same as the input value. In a thresholded LUT, output values are mapped to zero for all input values below the threshold, while output will be the same as input for values above the threshold. For example, if pixel intensities below 30 represent background fluorescence, then setting the threshold to 30 will force all pixels with values less than 30 to be zero, effectively decreasing background fluorescence without affecting the brighter values.

The software allows the user to select any threshold intensity level between zero and 255, and alters the values in the LUT accordingly. The user determines the threshold setting manually by viewing a well on the video monitor and adjusting the threshold value (through a menu) to a level at which the background is visibly black while all cells in the field are still visibly bright.

While a particular thresholding method is described herein, other forms of digital image manipulation, such as background subtraction, are also possible within the capacity of the present hardware and software configuration.

Analysis

The software provides for data analysis through the Analysis Menu, as shown in FIG. 8. The user can review the raw data file and mark any invalid data points which are not marked during the assay by selecting Edit Bad Data Points. In addition, means and standard deviations can be calculated and output in a format suitable for import by other software programs. The user selects the choice which corresponds to the manner in which the plate is loaded. For example, a 96-well plate might contain six different conditions such that each condition uses 16 wells in a pattern which is two across by eight down. The user would select number 1 from the menu, and the software program would calculate the means and standard deviations for the six groups and write these to the output file.

Quenching the Background Fluorescence

The dynamic range and accuracy of viable cell number measurements can be enhanced by quenching the fluorescence in non-viable cells and the medium. Two dyes are used to treat the cell sample. The first is a fluorescent dye that accumulates in viable cells only. Although such a dye also enters dead cells, it leaks out from the non-viable cells due to loss of membrane integrity and therefore does not significantly accumulate in dead cells. The concentration of the dye in dead cells is no more than two times its concentration in the medium. The first dye may be, for example, an ester of fluorescein or related dyes which are lipophilic, apolar, and cross the cell membrane. Non-specific esterases inside the cell hydrolyze the ester dye to a non-ester anionic dye which is trapped inside the cell if the cell is viable and has an intact membrane. Since dead cells leak the dye back out, only viable cells become brightly fluorescent.

The second dye used to quench the fluorescence of the first dye is a dye that enters dead cells but not viable cells. The second (quenching) dye may be, for example, an acid dye typically used for "dye exclusion" tests, such as trypan blue, eosin Y, Acid Black 2 (a dye in the nigrosin family), direct yellow 59 and primuline yellow (primulin). In dye exclusion tests, these dyes are substantially excluded by viable cells but can enter the membranes of dead cells, thereby staining them. The levels of such dyes inside viable cells are, for example, at least 1000 times lower than their concentrations in the medium. The second dye may quench the fluorescence of the first dye by, for example, being in close proximity of the first dye, or binding to the first dye.

EXAMPLES

The examples described below illustrate the performance of the preferred embodiment of the present invention. In examples 1–3, cells were stained with fluorescein diacetate (FDA) and treated with eosin Y to quench background fluorescence in non-viable cells. In example 4, cells were stained with calcein-AM and treated with trypan blue to quench background fluorescence.

For examples 1–3, fluorescent dye solutions and assays were prepared as follows.

Fluorescein diacetate (FDA) (Sigma Chemical Co., St. Louis, Mo.), or 2',7'-bis-(2-carboxyethyl)-5(and-6) carboxyfluorescein, acetoxymethyl ester (BCECF-AM) (Molecular Probes, Inc., Eugene, Oreg.) was dissolved in dimethyl sulfoxide (DMSO) to produce a 1 mg/ml stock solution. The stock was filtered through 0.8 µm nylon, aliquoted into 1.5 ml microfuge tubes and stored frozen at −20° C. in the dark. For individual assays, an intermediate stock was prepared by thawing and diluting an aliquot with RPMI-1640+10% Fetal Calf Serum (FCS) such that adding 50 µl of dye solution to a well would produce a final concentration of 8 µg/ml. To minimize reaction with endogenous enzymes in the FCS (which could increase the background fluorescence by cleaving ester groups to form free fluorescein), intermediate dilutions were prepared immediately prior to loading each individual plate.

Hoechst 33342 (Calbiochem, San Diego, Calif.) was dissolved in double distilled water to produce a 1 mg/ml stock solution, 0.8 µm filtered, and stored in 1.5 ml microfuge tubes in the dark at 4° C. For individual assays, an intermediate stock was prepared by diluting an aliquot with RPMI-1640+10% FCS such that delivery of 50 µl would produce a final concentration of 10 µg/ml in the well. Hoechst 33342 was more stable than FDA and BCECF-AM, and did not need to be mixed separately for each individual plate.

The 1.0% (w/v) solution of eosin Y (Sigma Chemical Co., St. Louis, Mo.) in 0.9% NaCl was stored at room temperature.

Cell lines used were the human neuroblastoma cell line SMS-KCNR and the BA-1 hybridoma cell line. Cell lines are grown in a $CO_2$ incubator in RPMI-1640+10% FCS. SMS-KCNR cells were removed from the tissue culture flask by washing and incubating in a monolayer of Puck's EDTA for 10 minutes. BA-1 cells grow in suspension and were collected by centrifugation. Cells were then pipetted to break up clumps, centrifuged and counted by hemacytometer and trypan blue exclusion.

Example 1

Figure 9:
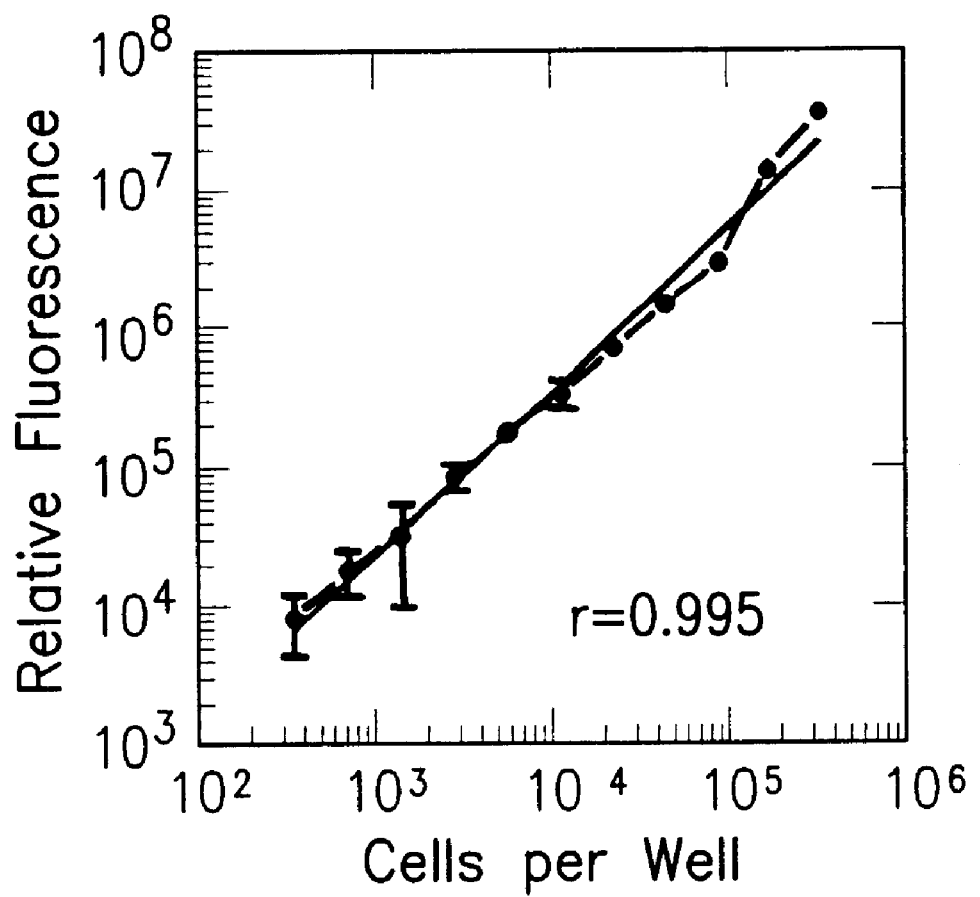
FIG. 9 shows the results from example 1, initial serial dilution tests.

Initial tests for the linearity and sensitivity of the preferred embodiment of the fluorescence digital imaging microscopy system were performed on cells which were treated with dye separate from the 96-well plate, to minimize any effects from loading dye in situ. BA-1 hybridoma cells (which grow as a single cell suspension) were incubated with BCECF-AM in a test tube and rinsed with RPMI-1640+10% FCS prior to loading in a 96-well plate. FIG. 9 shows the serial dilution curve. Fluorescence at 4× magnification was very linear over a range from 340 cells/well through 350,000 cells/well ($3.4 \times 10^3$ cells/ml to $3.5 \times 10^6$ cells/ml), with a coefficient of linearity equal to 0.995. The system provided excellent linearity covering approximately 3 logs of fluorescence and 3 logs of cell density.

Example 2

Figure 10:
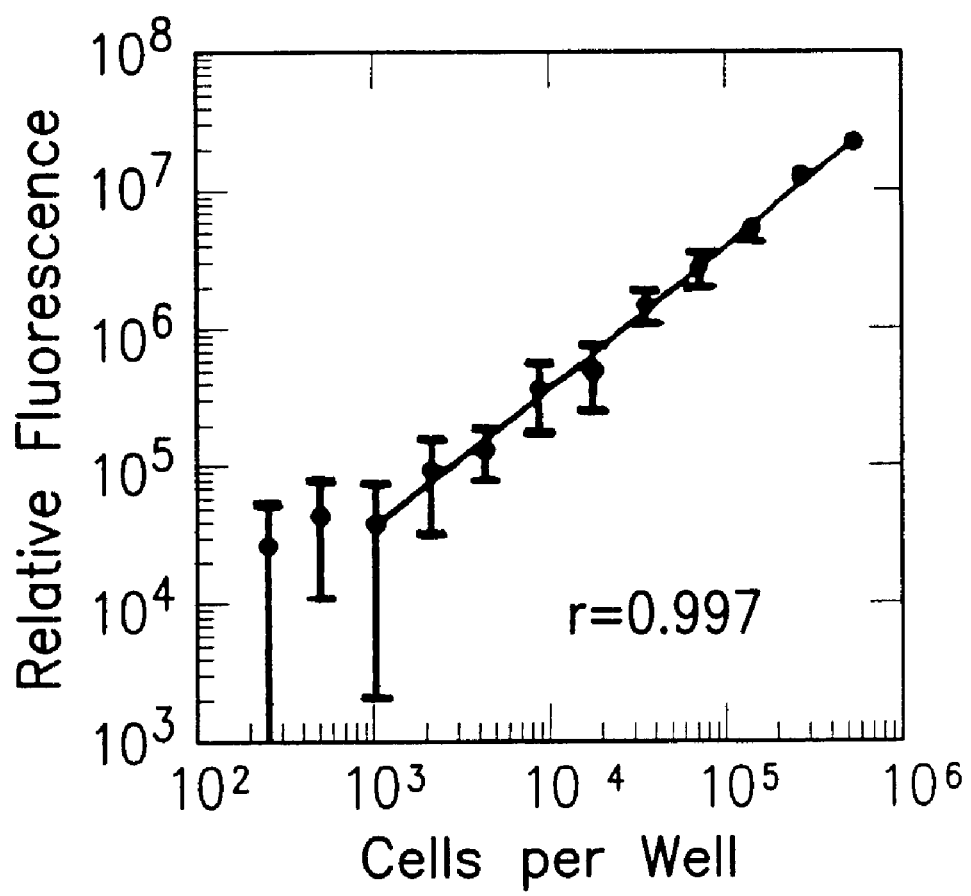
FIG. 10 shows the results from example 2, in situ serial dilution tests.

For initial testing of in situ linearity, Hoechst 33342 dye was used because it produces minimal background fluorescence. FIG. 10 shows a typical dilution curve for SMS-KCNR, a neuroblastoma cell line, in RPMI-1640+10% FCS treated in situ with Hoechst 33342 (10 µg/ml for 30 min. at 37° C.) in a 96-well plate and scanned at 4× magnification without an image intensifier. Good linearity (r=0.997) was seen from $1 \times 10^3$ cells/well to $5.4 \times 10^5$ cells/well ($1.0 \times 10^4$ cells/ml to $5.4 \times 10^6$ cells/ml). Results were equally good at magnifications of 10× and 4× with image intensification, producing coefficients of linearity of 0.997 and 0.994 respectively.

Example 3

Eosin Y Treatment of Samples Containing Large Numbers of Non-Viable Cells

Serial dilution of viable cells. For studies of the correlation of relative fluorescence and viable neuroblastoma cell number, cells were loaded in Falcon 96-well tissue culture plates (Becton-Dickinson, Lincoln Park, N.J.) with an Electrapette multi-channel pipettor (Matrix Technologies, Lowell, Mass.) set for serial twofold dilution mixing 125 µl volume in 3 cycles. One million cells per well to two cells per well were plated in 8 replicate wells per condition. Final well volume was 125 µl. Neuroblastoma cells were allowed to settle and attach for 2–8 hours. Prior to scanning, the tissue culture plates were gently loaded by multi-channel pipettor with 50 µl per well of intermediate FDA stock and incubated at 37° C. for 30 minutes. After incubation, plates were loaded with 30 µl per well of 0.5% eosin Y solution, yielding final eosin Y concentration of 0.083%; controls received a medium without eosin Y. Relative fluorescence was determined with the digital imaging microscopy system, using 4× magnification with image intensifier and Omega Optical XF22 filters.

Serial dilution of viable cells with additional dead cells. To study the influence of large numbers of dead cells on the ability of the digital imaging microscopy system to detect small numbers of viable cells, identical plates with serial fourfold dilutions of cells were prepared as before. Prior to staining with FDA, half of the plates were loaded with $4 \times 10^4$ of non-viable cells per well by removing 50 µl of media and replacing it with $4 \times 10^4$ dead cells resuspended in 50 µl of RPMI-1640 with 10% FCS. Non-viable cells for these experiments were obtained from the identical cell line, resuspended in RPMI-1640 with 10% FCS and frozen in 2° C. for 4 hours. Cell viability was determined after thawing by trypan blue dye exclusion counts to be less than 1%.

Figure 11A:
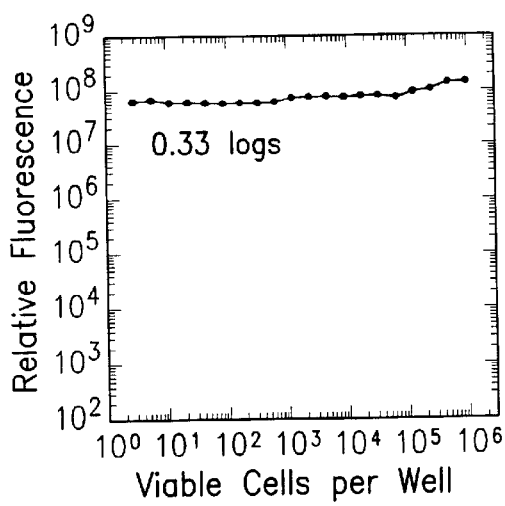
FIGS. 11 and 12 show the results from example 3, digital thresholding and eosin Y treatment.
Figure 11B:
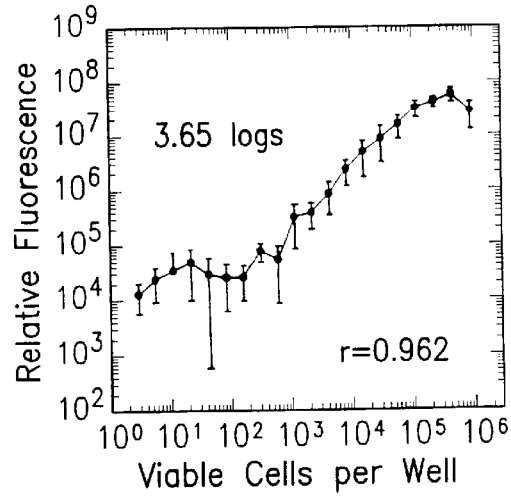
Figure 11C:
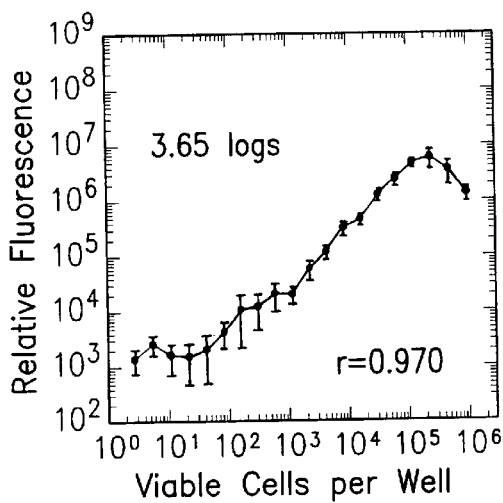
Figure 11D:
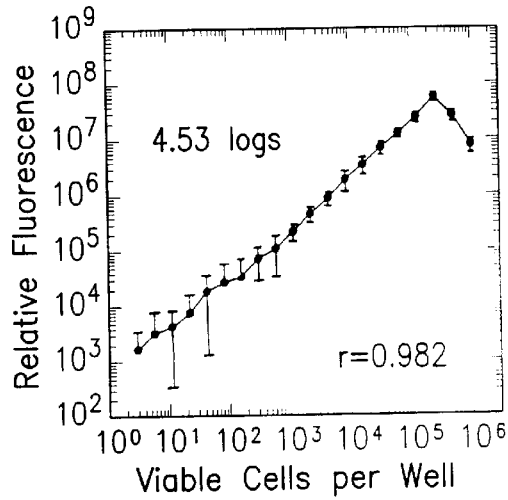
Figure 11E:
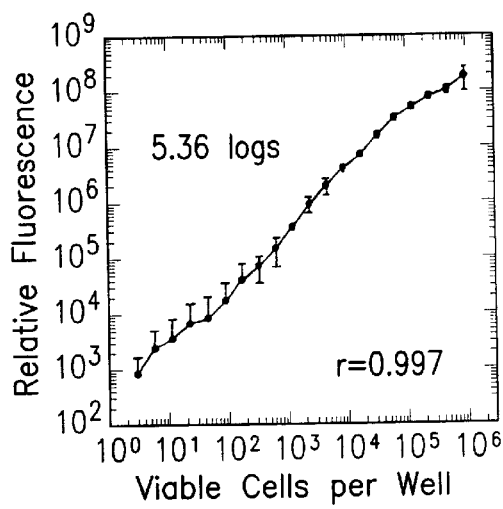

As shown in FIG. 11a, scans of FDA stained SMS-KCNR neuroblastoma cells produced a nearly flat curve with the digital imaging microscopy system using no method to reduce the background fluorescence across various cell concentrations, as fluorescence produced by the viable cells was obscured by background fluorescence in the medium. We analyzed replicate plates using digital image thresholding, the result of which is shown in FIG. 11b, and this decreased background fluorescence and allowed us to detect varying numbers of viable cells over 3.6 logs of dynamic range. Adding eosin Y to the sample markedly decreased background fluorescence without obscuring fluorescence from viable cells if used at a final concentration of 0.083%, as shown in FIG. 11c. The combination of both thresholding and eosin Y is shown in FIG. 11d, and the interference of background fluorescence was reduced, and the scan produced a linear increase in relative fluorescence intensity with increasing numbers of viable cells over nearly 5 logs. When the FDA concentration was 8 µg/ml, there was tapering off of fluorescence at cell densities above $1 \times 10^5$ cells/well, possibly due to exhaustion of the dye (FIGS. 11b, 11c, 11d). When the FDA concentration was increased to 12 µg/ml, scans were obtained with excellent linearity covering approximately 5 logs of fluorescence intensity and 4 logs of cell density (from $1 \times 10^6$ cells/well to $1 \times 10^2$ cells/well), as shown in FIG. 11e. The optimal concentration of FDA was dependent on the cell line used and the highest cell concentration in an assay, FDA concentrations>12 µg/ml increased background fluorescence, and concentrations from 8–12 µg/ml were found to be optimal.

Figure 12A:
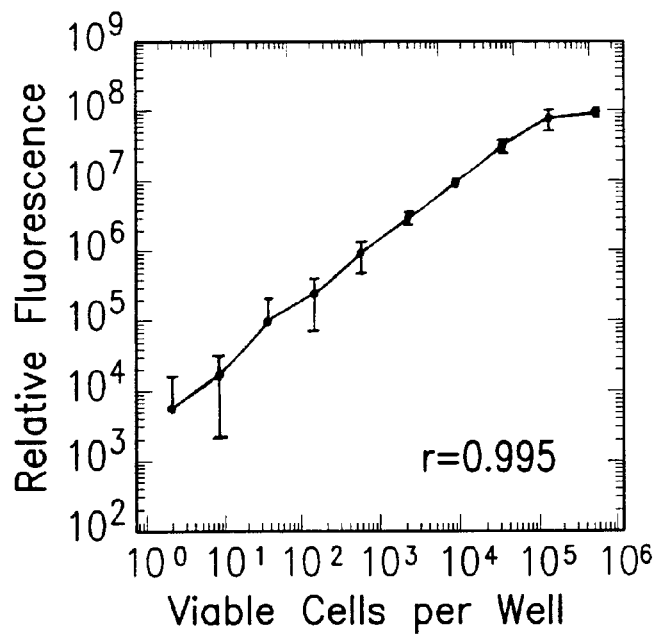
Figure 12B:
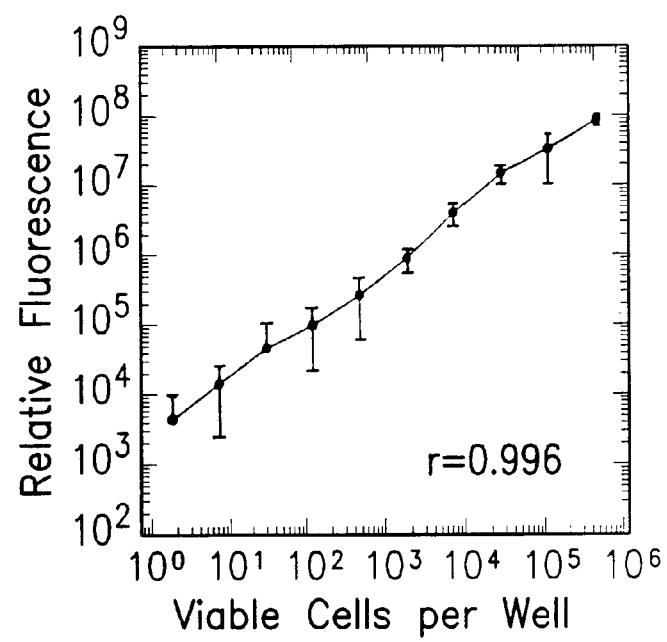

FIG. 12 shows the effectiveness of our background reduction method (combination of digital image thresholding and eosin Y addition), when a large excess of non-viable SK-N-SH neuroblastoma cells was added to the culture plates containing viable SK-N-SH cells prior to staining with FDA. Large numbers of non-viable cells could increase background fluorescence during a cytotoxicity assay by releasing esterases. Both control and test plates were stained and scanned with the digital imaging microscopy system under identical conditions. The control plates produced a linear increase in fluorescence intensity with increasing viable cell number, with the correlation coefficient equal to 0.995, as shown in FIG. 12a. The scans of a replicate plate with $4 \times 10^3$ additional non-viable cells/well produced a comparably linear relationship with the correlation coefficient equal to 0.996, and <10 viable cells/well were easily detected even in the presence of high numbers of non-viable cells, as shown in FIG. 12b.

Example 4

The performance of the fluorescence digital imaging microscopy system according to the present invention was demonstrated in an antibody dependent cellular cytotoxicity assay (ADCC). In this assay, tumor cells were stained with calcein-AM, a fluorescent dye similar to FDA. The tumor cells were mixed with effector cells at various effector to target (E:T) ratios. The effector cells in this case were human neutrophils, armed with a 15 micrograms/ml of anti-GD2 antibody. The monoclonal antibody bound by the fc portion to the fc receptors on the neutrophils, causing them to bind to the tumor cells (target cells) and kill them. Thus, there is a loss of calcein-AM fluorescence from the cells due to target cell lysis by neutrophils. The amount of killing is measured using the fluorescence digital imaging microscopy system, by measuring the amount of relative fluorescence in the sample (see FIG. 13).

Figure 13:
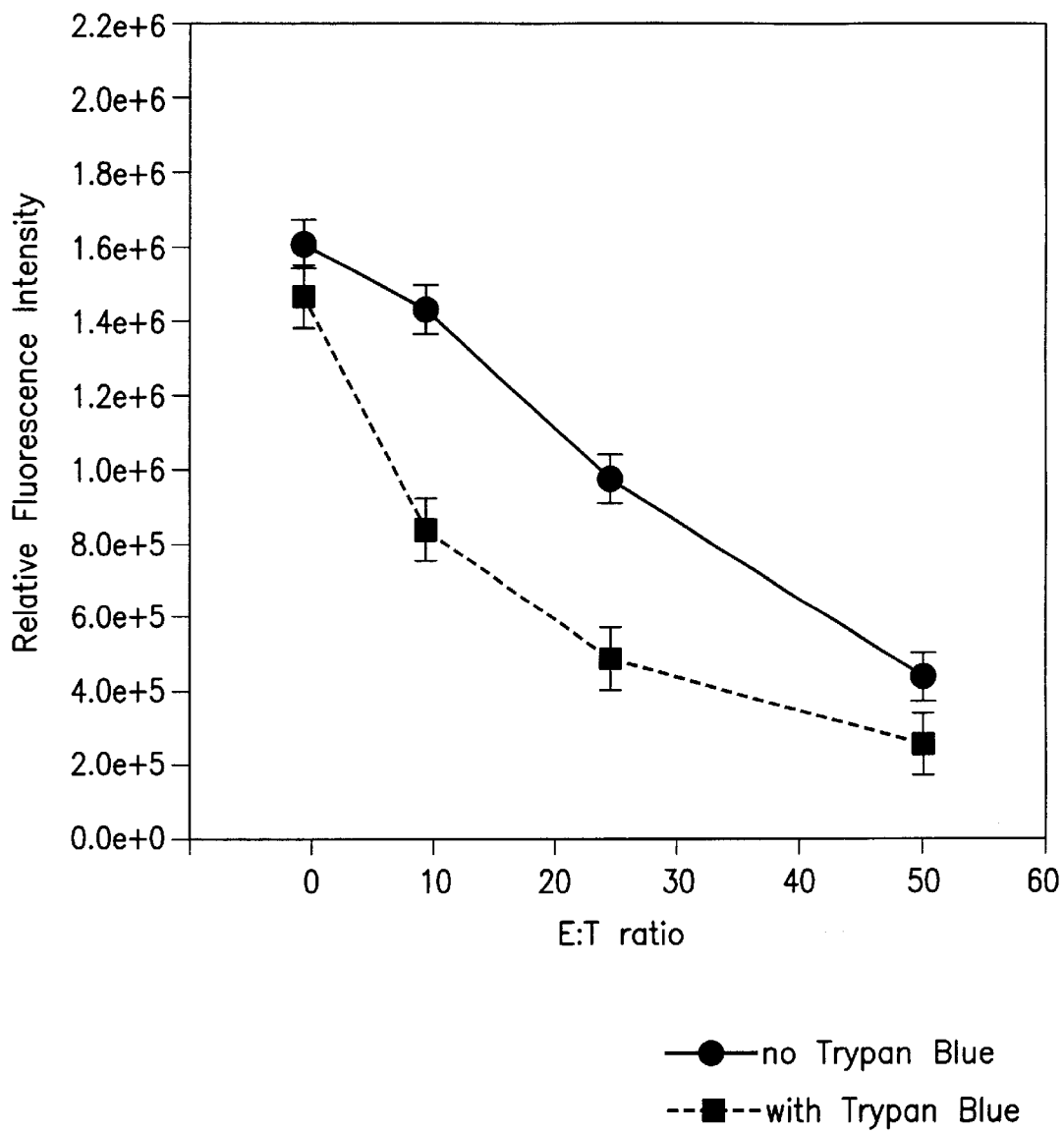
FIG. 13 shows the results from example 4, trypan blue treatment of tumor cells stained with calcein-AM.

Due to the existence of residual fluorescence in dead cells, the degree of cell killing is underestimated if the fluorescence from the dead cells is not distinguished from the fluorescence from the target cells. To increase the accuracy of the measurement, trypan blue was added to the assay to quench the residual fluorescence in dead cells. As shown in FIG. 13, the measured amounts of tumor cell killing are higher (i.e. the relative fluorescence intensity is lower) when trypan blue was added (the dashed curve with square dots) as compared to when no trypan blue was added (the solid curve with round dots).

The above examples describe using two dyes for staining the viable cells and for quenching background fluorescence in non-viable cells and the medium. Used with a fluorescence digital imaging microscopy system or other instruments that are suitable for quantifying fluorescence, this method enhances the dynamic range and accuracy of the viable cell number measurements. Although two specific dye combinations are described, other combinations may also be used.

In addition, although the chemical compounds are generally described as "dyes," the word "dye" is not intended to impart any positive limitation on the range of compounds that may be used in the described method, either in terms of chemical structure or in terms of chemical and physical properties.

It will of course be appreciated by those skilled in the art that the present invention is not limited to the precise embodiment disclosed. For example, various changes, alterations and modifications may be made to the hardware subsystems. It is also understood that although this application refers to multi-well tissue culture plates in describing the preferred embodiment, the stage and the scanning routine of the described embodiment can be modified to scan tissue culture containers of other shape or format, including individual dishes and flasks.

We claim:

1. A method for reducing background fluorescence in a culture cell sample during quantification of viable cell numbers using fluorescent dyes, comprising:

treating the sample with eosin Y, wherein the eosin Y enters non-viable cells but is substantially excluded by viable cells, wherein the background fluorescence in the medium and non-viable cells in the sample is quenched; and measuring an intensity of fluorescence of the treated sample.

2. The method of claim 1, wherein the sample is in a container, wherein the measuring step comprises recording a digital image of a defined area of the container using an imaging device, the digital image representing fluorescence light intensities of the defined area.

3. The method of claim 2, wherein the measuring step further comprises:

holding the container on a stage; and moving the stage and the imaging device relative to each other in at least two horizontal directions to image a plurality of areas.

4. The method of claim 3, further comprising quantifying relative cell numbers in the sample.

5. The method of claim 4, wherein the quantifying step comprises manipulating digital images to reduce background fluorescence intensities in the images and acquiring information relating to relative cell numbers.

6. A method for reducing background fluorescence in a culture cell sample during quantification of viable cell numbers using fluorescent dyes, comprising:

treating the sample with eosin Y, wherein the sample is in a container, wherein the eosin Y enters non-viable cells but is substantially excluded by viable cells, wherein the background fluorescence in the medium and non-viable cells in the sample is quenched;

measuring an intensity of fluorescence of the treated sample; and quantifying relative cell numbers in the sample.

7. The method of claim 6, wherein the measuring step comprises:

holding the container on a stage;

recording a digital image of a defined area of the container, the digital image representing fluorescence light intensities of the defined area;

moving the stage and an imaging device relative to each other in at least two horizontal directions to image a plurality of areas; and controlling the movement of the stage and imaging device and controlling the recording of the digital images, wherein the relative movements between the stage and imaging device and the recording of the images are performed in a synchronized manner and according to a predetermined scanning pattern.

8. The method of claim 7, wherein the measuring step further comprises inputting parameters according to a format of a container having multiple wells.

9. The method of claim 8, wherein the quantifying step comprises manipulating the digital images to reduce background fluorescence intensities in the images and acquiring information relating to relative cell numbers.

* * * * *

UNITED STATES PATENT AND TRADEMARK OFFICE

Certificate

Patent No. 6,665,430 B2                                Patented: December 16, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: C. Patrick Reynolds, Sherman Oaks, CA (US); Tomas Frgala, Brno (CZ); and Robert Proffitt, Cypress, CA (US).

Signed and Sealed this Twenty-Second Day of July 2008.

JAYANTI K. PATEL
*Supervisory Patent Examiner*
Art Unit 2619